(12) United States Patent
Pfauch et al.

(10) Patent No.: US 8,578,798 B2
(45) Date of Patent: Nov. 12, 2013

(54) PROBE SYSTEM FOR MEASURING A MEASURED VARIABLE OF FLUID CONTAINED IN A PROCESS CONTAINER, ESPECIALLY FOR STERILE APPLICATIONS

(75) Inventors: Thomas Pfauch, Leipzig (DE); Ingrid Wunderlich, Radebeul (DE)

(73) Assignee: Endress + Hauser Conducta Gesellschaft für Mess- und Regeltechnik mbH + Co., KG, Gerlingen (DE)

( * ) Notice: Subject to any disclaimer, the term of this patent is extended or adjusted under 35 U.S.C. 154(b) by 290 days.

(21) Appl. No.: 12/926,325

(22) Filed: Nov. 10, 2010

(65) Prior Publication Data

US 2011/0107857 A1    May 12, 2011

(30) Foreign Application Priority Data

Nov. 11, 2009 (DE) .......................... 10 2009 046 637

(51) Int. Cl.
*G01D 11/30* (2006.01)
(52) U.S. Cl.
USPC ....................................................... 73/866.5
(58) Field of Classification Search
USPC ....................................................... 73/866.5
See application file for complete search history.

(56) References Cited

U.S. PATENT DOCUMENTS 5,011,587 A * 4/1991 Schmidt .......................... 204/401

FOREIGN PATENT DOCUMENTS

| DE | 197 23 681 C2 | 12/1998 |
|---|---|---|
| DE | 10 2005 036 865 A1 | 2/2007 |
| EP | 0 372 121 A1 | 6/1990 |
| WO | WO 2007/048821 A2 | 5/2007 |

* cited by examiner

*Primary Examiner* — Hezron E Williams
*Assistant Examiner* — Paul West
(74) *Attorney, Agent, or Firm* — Bacon & Thomas, PLLC

(57) ABSTRACT

A probe system for measuring a measured variable of a fluid, comprising: A probe body, which is connectable to the process container by means of a process connection; axially shiftable in a guiding passageway of the probe body between a measuring position and at least two different treatment positions; an immersion tube, which has a protective cylinder on its front end immersible in the fluid; a measuring probe held in the immersion tube, having a measuring head, wherein the measuring head is arranged within a region of the protective cylinder having openings; a first treatment chamber formed between the guiding passageway and the immersion tube; a second treatment chamber formed between the guiding passageway and the immersion tube and adjoining the first treatment chamber on a side of the first treatment chamber facing away from the process connection; and a seal arranged between the first and second treatment chambers, wherein the immersion tube has a first section with a first outer diameter and a second section adjoining the first section and having a second outer diameter smaller than the first outer diameter, so that, through axial shifting of the immersion tube, the seal arranged between the first and second treatment chambers can be opened.

9 Claims, 4 Drawing Sheets

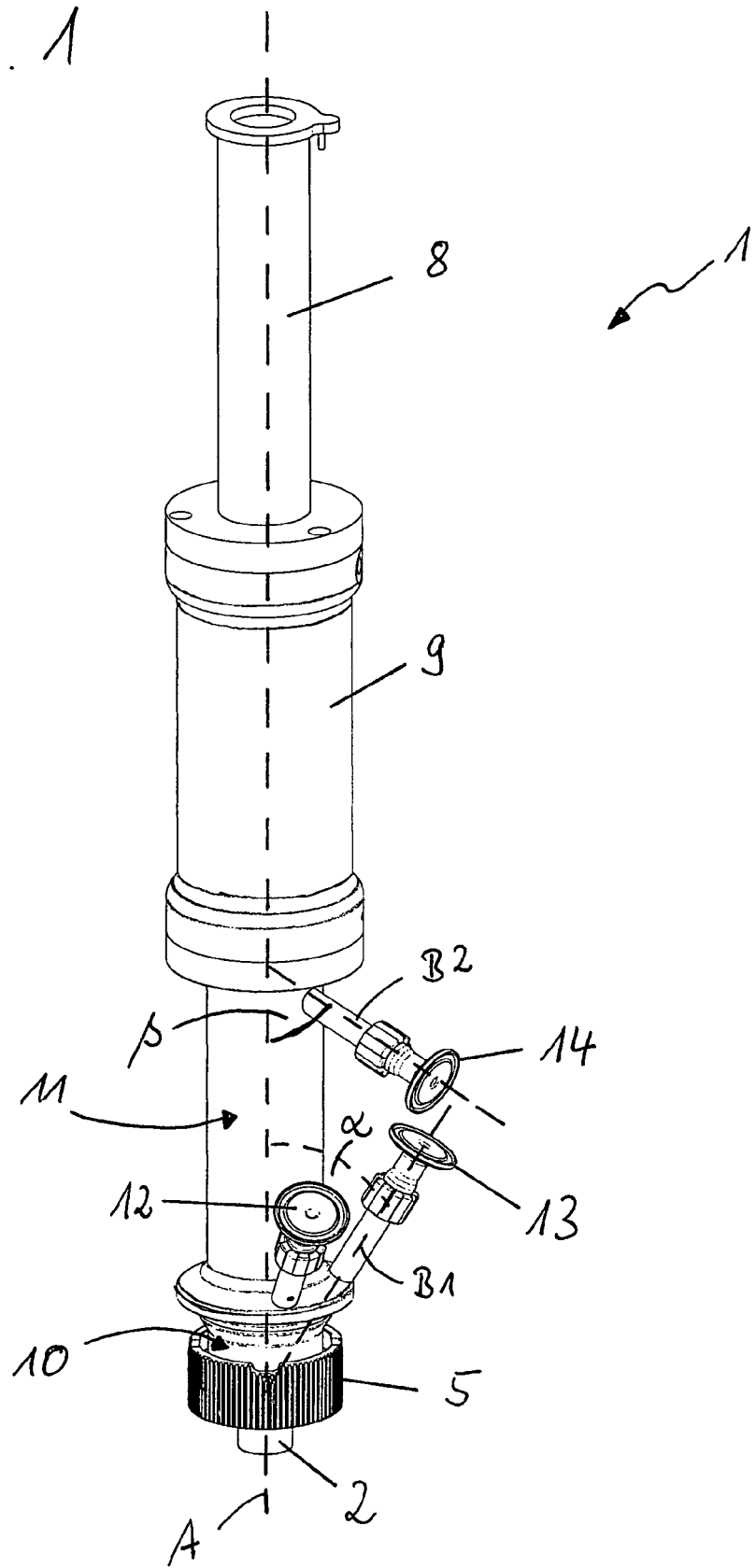

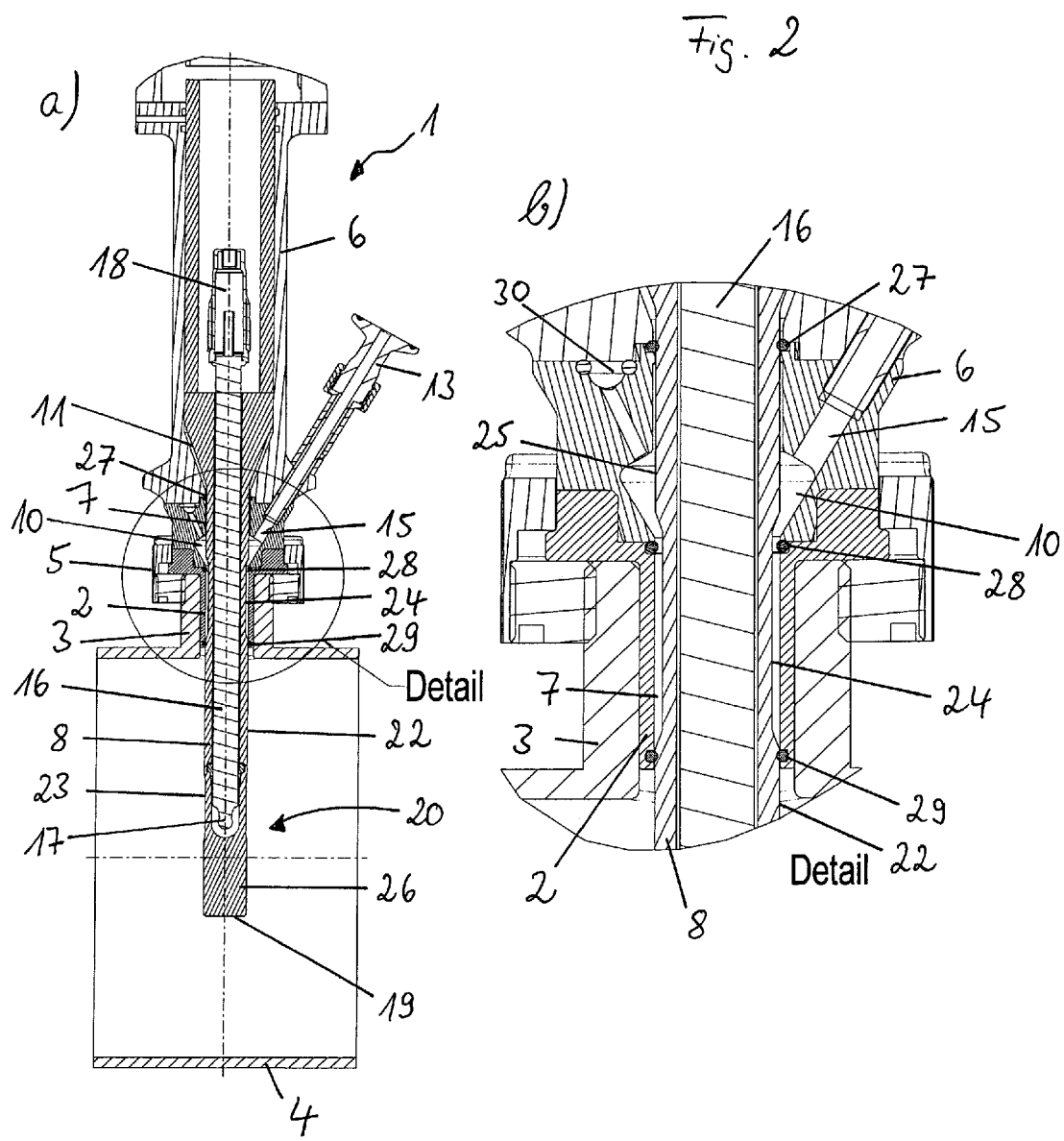

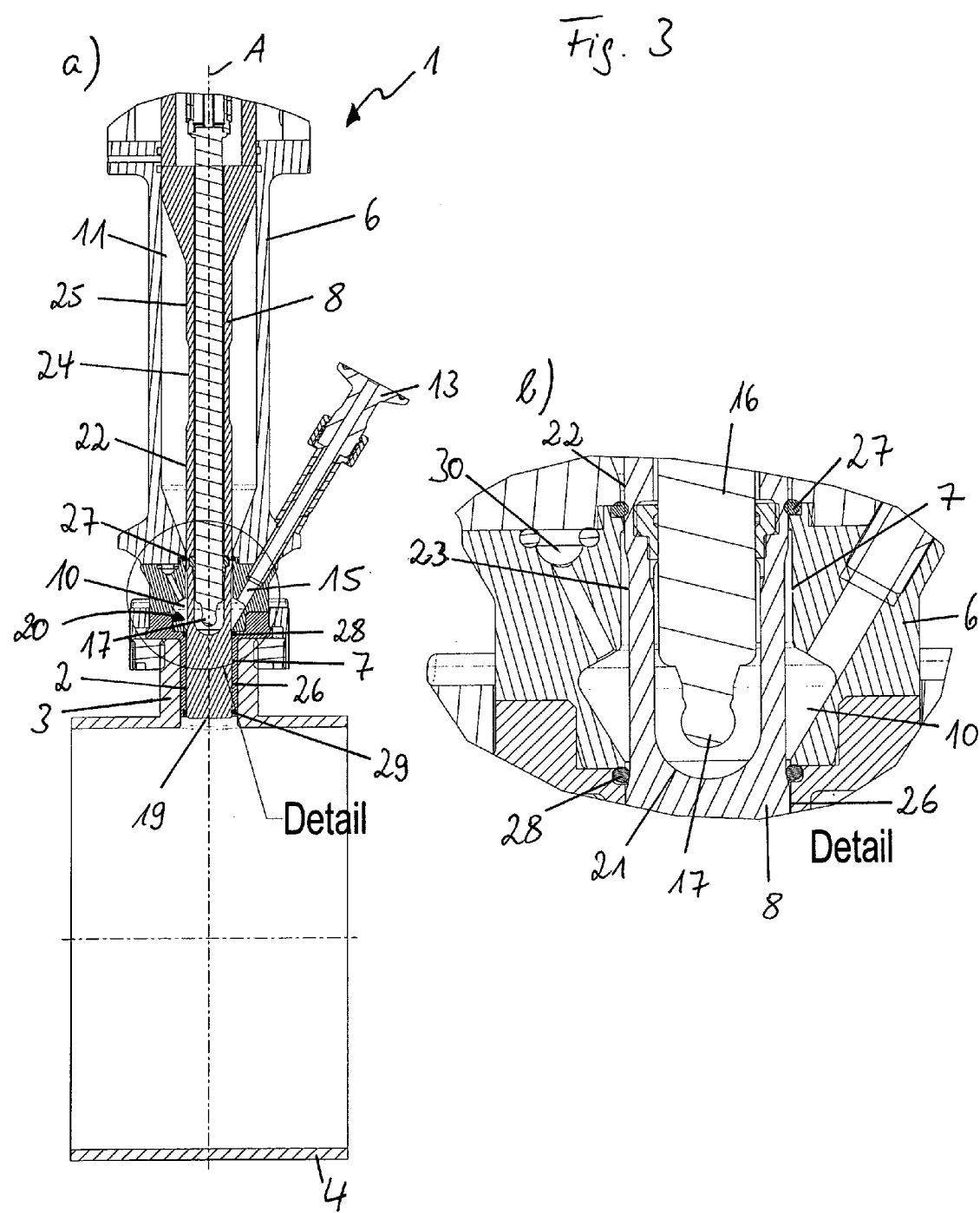

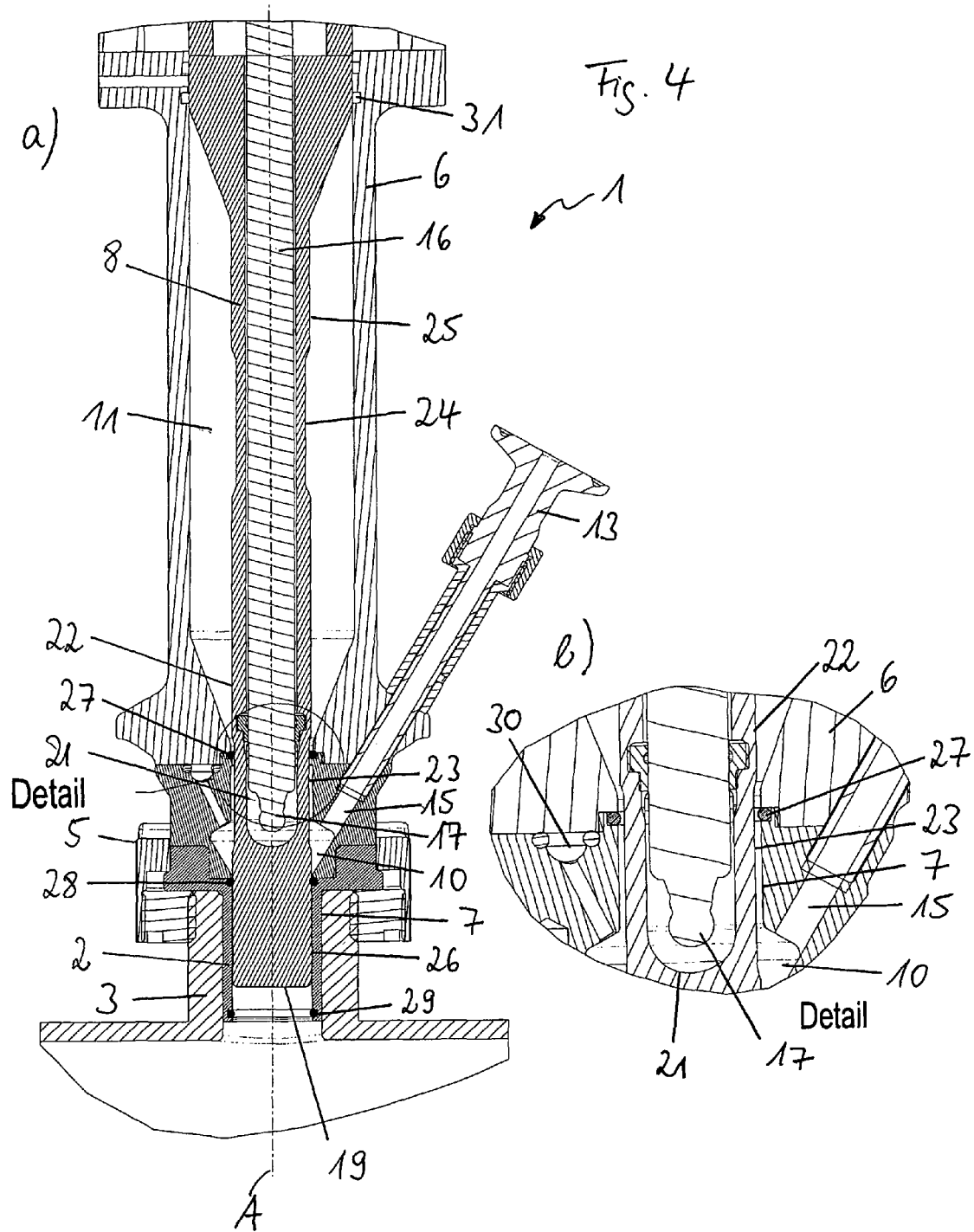

PROBE SYSTEM FOR MEASURING A MEASURED VARIABLE OF FLUID CONTAINED IN A PROCESS CONTAINER, ESPECIALLY FOR STERILE APPLICATIONS

TECHNICAL FIELD

The invention relates to a probe system for measuring a measured variable of a fluid contained in a process container, especially for sterile applications.

BACKGROUND DISCUSSION

The range of applications of probe systems for measuring physical or chemical, measured variables of a medium, e.g. of a fluid, especially a liquid, in process technology is numerous. For example, the manufacture of sterile solutions in pharmaceutical or food processes requires the use of measuring probes for monitoring the product, or the process. The measuring probes can be pH measuring probes, conductivity measuring probes, optical or electrochemical measuring probes for determining a concentration of a substance contained in the medium to be monitored, e.g. a substance such as $O_2$, $CO_2$, certain ion types, organic compounds.

From the state of the art, it is known to perform an inline-measuring of fluids, e.g. products of chemical processes, in the case of which probe systems with axially movable immersion tubes, in which a measuring probe is held, are used. Such probe systems are also referred to as "retractable assemblies". These retractable assemblies are secured on a process container, for example, a pipe conveying the fluid to be monitored by measuring, and include a treatment chamber, into which the measuring probe can be moved by means of the immersion tube temporarily during operation for calibration- or washing, and/or rinsing, purposes and therein brought in contact with a calibration liquid and/or with a washing, and/or rinsing, medium for cleaning. When the calibration-, or washing, and/or rinsing, procedure is finished, the measuring probe can, thereafter, be moved back into the fluid to be monitored, in order to continue with the inline measuring. In such case, contamination of the monitored fluid with calibration liquid, or, conversely, a contamination of the calibration liquid with fluid being monitored is counteracted with the assistance of seals, which seal the treatment chamber and the process container relative to one another.

For retractable assemblies for use in sterile processes, it has been suggested to provide a second treatment chamber. Thus, for example, in DE 38 20 405 C2, a retractable assembly is described, which has a housing with a housing nozzle connectable to a reaction vessel, wherein, in the housing, there is an immersion tube with a measured value sensing probe, whose measuring head is surrounded by a cage with passageways. The immersion tube can be viewed axially from a measuring position out of the housing nozzle into a retracted rest position in the housing, and back again into the measuring position. In the rest position, the opening of the housing nozzle is sealed by means of a closure. In the rest position, the front part of the immersion tube with the measuring head of the probe facing the reaction vessel is located in a first washing and/or rinsing chamber of the housing, which has an inlet and a drain. Associated with the rinsing chamber in the housing is a second rinsing chamber, further remote from the reaction vessel and having its own inlet and its own drain. In the rest position, a washing and/or rinsing and/or sterilizing of the measuring probe and of parts of the immersion tube can be performed by sending wash-, rinse-, or sterilization medium through the first and the second rinsing chambers. In this way also, those parts of the immersion tube and/or the probe can be cleaned and sterilized, which, in the case of the out viewing of the probe into the measuring position come into the first rinsing chamber. Therewith, it should be prevented, that not washed, or rinsed, and sterilized parts of the immersion tube and the probe come into the rinsing chamber, in which, in given cases, medium of the reactor vessel is contained, and cause contamination.

The drain of the second rinsing chamber is connected with the inlet of the first rinsing chamber via a liquid transport line, so that wash-, rinse- or sterilization medium introduced into the second rinsing chamber goes further via the liquid transport line and the inlet of the first washing and/or rinsing chamber into the first washing and/or rinsing chamber and from there via the drain of the first rinsing chamber is fed to a condensate drain or to a wash, or rinse, drain. This construction does, however, not permit supplying only a single rinsing chamber with liquid.

Between the first and second rinsing chamber in the case of the retractable assembly described in DE 38 20 405 C2, a seal is arranged, which seals the two washing, and/or rinsing, chambers relative to one another. In the region of this seal, no sufficient cleaning, or sterilization of the immersion tube is assured. Especially, also the seal itself cannot be sufficiently cleaned or sterilized.

Also in German patent application DE 10 2005 051 279 A1, a retractable assembly for use in sterile processes is described. Such an assembling includes a housing, which has a space for accommodating a measuring probe and a first chamber for accommodating a first fluid, e.g. a calibration fluid or a washing, and/or rinsing, fluid. The first chamber is in communication with the space for accommodating the probe. The housing includes furthermore a connecting section, by means of which the housing is connectable, or in connection, with a container, which serves for accommodating a medium, whose property is to be measured with the probe. In the housing, there is at least a second chamber for accommodating a second fluid, which should be uncritical both relative to the first fluid as well as also relative to the medium. An example of a second fluid is sterile water. The second chamber is arranged between the first chamber and the connecting section of the housing. In the case of defective seals, so should the probability for a contamination of the medium by the first fluid as well as also a contamination of the first fluid by the medium be lessened.

The probe is accommodated in an immersion tube, in which openings are provided for access of the medium, or a rinsing liquid, to the measuring head. The probe can be moved axially within the housing between a measuring position, in which the probe with its measuring head surrounding a sensor protrudes inwardly into the medium and a washing, and/or rinsing, position, in which the measuring head is arranged within the first rinsing chamber. In order also in the washing, and/or rinsing, position to assure a sealing of the second rinsing chamber arranged between the first rinsing chamber and the medium relative to the medium, the distance between the front end of the probe and the openings in the region of the measuring head of the probe must be greater than the axial length of the second rinsing chamber, i.e. than the distance between the two seals, which seal the second rinsing chamber from medium, on the one hand, and from the first rinsing chamber, on the other hand. As a result, this brings about that, for a certain immersion depth of the measuring head in the medium in measurement operation, a stroke of the immersion tube must be produced, which is enlarged by the axial length of the second rinsing chamber. Additionally, the front end of the immersion tube reaching beyond the position of the actual measuring head by, thus, this length requires correspondingly much space, so that the retractable assembly can only be applied to process containers having a certain minimum volume.

An object of the invention is to provide a probe system of the initially described type, which permits a calibrating of the measuring probe and/or a sufficient sterilizing of the immersion tube and the measuring probe in the state secured on the process container.

SUMMARY OF THE INVENTION

This object is achieved by a probe system for measuring a measured variable of a fluid, especially a liquid, contained in a process container, wherein the probe system comprises: a probe body, which is connectable to the process container by means of a process connection, axially shiftable in a guiding passageway of the probe body between a measuring position and at least two different treatment positions, an immersion tube, which has on its front end immersible in the fluid a protective cylinder; a measuring probe held in the immersion tube, the measuring probe having a measuring head, wherein the measuring head is arranged within a region of the protective cylinder having openings; a first treatment chamber formed between the guiding passageway and the immersion tube, and a second treatment chamber formed between the guiding passageway and the immersion tube and adjoining the first treatment chamber on a side of the first treatment chamber facing away from process connection; and a seal arranged between the first and the second treatment chambers wherein the immersion tube has a first section with a first outer diameter and a second section following the first section and having a second outer diameter smaller than the first outer diameter, so that, through axial shifting of the immersion tube, the seal arranged between the first and the second treatment chambers can be opened.

The seal effects an isolation of the two treatment chambers from one another, so that the treatment chambers can, in each case, be washed, or rinsed, individually with a fluid. Especially, the first treatment chamber, in a treatment position, in which the measuring head of the measuring probe is arranged within the first treatment chamber, can be washed, or rinsed, with a calibration liquid, which comes in contact also with the measuring head via washing, and/or rinsing, openings of the protective cylinder formed in the immersion tube. In this way, a calibrating of the measuring probe is possible. Through opening of the seal arranged between the first and the second treatment chambers, the two treatment chambers are connected with one another. Through supplying of a rinse- or sterilization fluid into the connected treatment chambers, all parts of the immersion tube and the measuring probe arranged in the two chambers, even those arranged in the region of the seal can then be cleaned, or sterilized. Also the opened seal can then be sterilized.

The measuring head comprises the primary measuring transducer of the measuring probe. For example, the measuring head can comprise a pH-value-sensitive, glass membrane of a pH glass electrode, an ion selective membrane an ion selective electrode, an ion sensitive semiconductor electrode of an ISFET-sensor, a membrane of an amperometric sensor, a temperature sensor, a washing, and/or rinsing, arrangement of an inductive conductivity sensor, an electrode arrangement of a conductive conductivity sensor or a pressure sensor.

The guiding passageway can comprise axial sections of different cross section. Thus, the first treatment chamber between the guiding passageway and the immersion tube can be formed, wherein the guiding passageway in the region of the first measuring chamber can comprise a widened axial section. Also the second treatment chamber can be formed between an at least partially cross sectionally widened section of the guiding passageway and the immersion tube.

In an embodiment of the probe system, the second section of the immersion tube adjoins the first section in the direction of the front end, wherein, in a first treatment position of the immersion tube, the seal seals the first treatment chamber and the second treatment chamber relative to one another, and in the case of an axial shifting movement of the immersion tube in a direction facing away from the process connection into a second treatment position, the seal is opened, and a fluid passageway is formed between the first and second treatment chambers.

Both in the first as well as also in the second treatment positions, the measuring head is retracted into the probe body, especially into the first treatment chamber, and the first treatment chamber is sealed relative to the process container. In the measuring position, the immersion tube is moved so far out from the probe body in the direction the process container, that the measuring head is arranged within the process container and immersed into the fluid, whose measured variable is to be determined.

The probe system can be placed in a first treatment position, in the case of which the first treatment chamber is sealed relative to the process container and relative to the second treatment chamber. Within this relatively small space, a washing, or rinsing, of the measuring head and/or a calibrating of the measuring probe can occur, in the case of which, in each case, only a small amount of wash- and/or rinse-, or calibration medium is required. In the case of an axial shifting of the immersion tube in the direction facing away from the process connection, due to the smaller outer diameter in the second section of the immersion tube, the seal between the first and second treatment chambers is opened. Therefore, in the second treatment position of the immersion tube, or the measuring probe, the first and second treatment chambers are connected with one another via a gap between the immersion tube and the guiding passageway at the originally sealed location, so that the retracted immersion tube can be supplied over its entire length arranged within the first and second treatment chambers with a wash- and/or rinse- or sterilization medium, without the seal arranged between the two chambers hindering the sterilization, or cleaning of the immersion tube. In this position, moreover, also the seal is washable, or rinseable, or sterilizable.

In an embodiment, the seal is formed by a first sealing element arranged within the guiding passageway, for example, an O-ring arranged within an encircling annular groove or a shaped seal, wherein the first sealing element in the first treatment position of the immersion tube lies against its first section with the first outer diameter. In the second treatment position, in the case of an axial movement of the immersion tube in the direction facing away from the process connection, the second section of the immersion tube is brought to the sealing element, so that between the sealing element and the second section of the immersion tube, due to its smaller second outer diameter relative to the first outer diameter, a gap is opened, which connects the first and second treatment chambers with one another.

The probe system can include, furthermore, at least two fluid lines, which open into the first treatment chamber, of which one serves as supply line and another as drain line, as well as, opening into the second treatment chamber, a fluid line, which serves selectively as supply line- or drain line. If the measuring head is arranged in the first treatment chamber in the first treatment position of the immersion tube, then, via the supply line opening into the first treatment chamber, a wash, rinse, sterilization or calibration medium can be introduced into the first treatment chamber, and, via the drain line likewise opening into the first treatment chamber, then drained out.

Preferably, the fluid lines, which open into the first treatment chamber, are embodied as bores within the probe body, and have an inclination relative to the longitudinal axis of the probe body, or the longitudinal axis of the immersion tube. For example, the bore axis can form with the longitudinal axis of the probe body an angle of 20° to 80°, wherein the vertex of such angle points toward the process connection. An orientation of the bores inclined in such a manner permits an installation space saving arrangement of washing, and/or rinsing, connections to the bores.

The fluid line serving selectively as supply line- or drain line, opening into the second treatment chamber, is preferably the only fluid line opening into the second treatment chamber. It can likewise be embodied as a bore placed within the probe body and having an inclination relative to the axis of the immersion tube. For example, the bore axis of the fluid line can form with the longitudinal axis of the probe body an angle of 20° to 80°, wherein the apex of such angle points away from the process connection.

The supply line and/or the drain line, which opens into the first treatment chamber, can be closable by means of a valve. In such case, the valve of one of the two fluid lines can automatically be closed when the immersion tube is moved into the second treatment position, for example, via an electronic control unit, which also controls the immersion tube movement of the probe system. In this way, washing and/or rinsing liquid or sterilization medium can be introduced via the fluid line opening into the second treatment chamber, and then drained out via the correspondingly not closed fluid line opening into the first treatment chamber. Alternatively, also via the fluid line not closed by means of valve, washing and/or rinsing liquid or sterilization medium can be introduced into the first treatment chamber and drained via the fluid line opening into the second treatment chamber.

In this embodiment, in contrast to the retractable assemblies known from the state of the art, only three openings are required for the supply- and drain lines for calibration-, wash-, rinse- and sterilization media, which simplifies the total structure of the probe system.

In an additional embodiment, some or all of the fluid lines opening into the first and second treatment chambers are provided with connection nozzles for the connection of one or a plurality of external reservoirs of wash-, rinse-, calibration and/or sterilization media, wherein all connection nozzles are arranged on one side of an imaginary longitudinal section plane through the probe body, extending not on the longitudinal axis of the probe body, but, however, parallel thereto. This has the advantage that the connection nozzles are accessible from a single side of the probe system, so that the oppositely lying side remains free as installation space.

In an additional embodiment of the probe system, on the side of the first treatment chamber facing the process connection, a second seal is arranged, which seals the first treatment chamber relative to the process container, when the immersion tube is located in the second treatment position. Optionally, the first treatment position can be so selected, that the second seal also seals the first treatment chamber relative to the process container, when the immersion tube is located in the first treatment position. Spaced from the second seal on the process connection side, end region of the probe body, a third seal can be arranged, which seals the guiding passageway and the first treatment chamber relative to the process container, when the immersion tube is located in the measuring position or the first treatment position. The distance between the second and the third seal is preferably greater than the axial diameter of the washing, and/or rinsing, openings of the immersion tube.

Such an arrangement of two seals lying behind one another, between the first treatment chamber and the measurement fluid, has two advantages: On the one hand, in the case of an axial movement of the immersion tube, in the case of which the washing, and/or rinsing, openings, in each case, slip over one of the seals, the, in each case, other seal serves to assure a sealing of the first treatment chamber relative to the process container in each position of the immersion tube. On the other hand, in this manner, the two seals are, in each case, one after the other, washed and/or rinsed and/or sterilized, without that the probe system must be removed from the process. The second seal can even be washed and/or rinsed and/or sterilized while the process is running.

In the case of an embodiment of the probe system advantageous for the sterilizing of the second seal, there adjoins on the first section of the immersion tube with the first outer diameter on its side facing away from the front end of the immersion tube a third section of the immersion tube, which has, relative to the first outer diameter, a smaller, third outer diameter, wherein the third outer diameter is, especially, equally as large as the second outer diameter, i.e. as the outer diameter of the second section of the immersion tube, so that, through an axial shifting of the immersion tube in the direction of the process connection into the measuring position, the second seal is opened.

The second seal can be formed, for example, by a second sealing element arranged within the guiding passageway, for example, an O-ring or a shaped seal arranged in an annular groove, wherein the sealing element in the second treatment position lies against the first section of the immersion tube, while, in the case of an axial movement of the immersion tube toward the process connection into the measuring position of the immersion tube, between the second sealing element and the third section of the immersion tube, a gap is opened, which makes the second sealing element accessible for liquid supplied via the supply line into the first treatment chamber.

In this way, wash-, rinse- or sterilization medium from the first treatment chamber can reach the second sealing element via the gap and so enable a washing, rinsing or sterilization of the second sealing element, while the measuring probe is located in the measuring position in the process container and immersed in the fluid to be monitored.

The third section has, preferably, an axial length, which is larger than the axial distance between the second and the third seal, i.e. between the two seals arranged lying behind one another, between the first treatment chamber and the measurement fluid.

Adjoining the third section of the immersion tube on its side facing away from the front end can be a fourth section of the immersion tube, whose outer diameter corresponds to that of the first section, and is, thus, larger than the outer diameter of the third section. If the immersion tube is located in measuring position, then the third sealing element, which is arranged within the guiding passageway nearest to the process connection side end of the probe body, lies against the first section of the immersion tube. The sealing element arranged between the first and second treatment chambers lies simultaneously against the fourth section of the immersion tube, while there remains between the second sealing element and the third section of the immersion tube a gap, which can be accessed by wash-, rinse- or sterilization medium. Through supplying of wash-, rinse- or sterilization medium into the first treatment chamber in this position of the immersion tube, the first treatment chamber, the second sealing element and the gap between immersion tube and guiding passageway in the region of the third section of the immersion tube can be washed, rinsed and/or sterilized.

The previously described probe system permits a large number of treatment steps of the measuring probe held in the immersion tube, while the probe system is secured on a process container. Thus, a possible method for operating such a probe system, whose immersion tube can be shifted axially into a measuring position, a first treatment position and a second treatment position, comprises the steps of:
- shifting of the immersion tube into the second treatment position, in which the seal between the first and second treatment chambers is opened, so that the first and second treatment chambers are connected with one another;
- securing a measuring probe within the immersion tube, while the immersion tube is located in the second treatment position;

as well as at least one of the steps of:
- supplying a sterilization medium into the connected treatment chambers and sterilizing the sections of the immersion tube located within the first and second treatment chambers and the measuring head of the measuring probe accessible via the washing, and/or rinsing, openings within the protective cylinder on the front end of the immersion tube while the immersion tube is located in the second treatment position;
- supplying a sterilization medium into the first treatment chamber and sterilizing the section of the immersion tube located within the first treatment chamber and the measuring head of the measuring probe accessible via the washing, and/or rinsing, openings within the protective cylinder on the front end of the immersion tube while the immersion tube is located in the first treatment position, in which the first and second treatment chambers are sealed relative to one another;
- supplying a washing, and/or rinsing liquid into the first treatment chamber and washing and/or rinsing the section of the immersion tube located within the first treatment chamber and the measuring head of the measuring probe accessible via the washing, and/or rinsing, openings within the protective cylinder on the front end of the immersion tube while the immersion tube is located in the first treatment position;
- supplying a calibration liquid into the first treatment chamber and calibrating the measuring probe, whose measuring head is supplied with calibration liquid via the washing, and/or rinsing, openings within the protective cylinder on the front end of the immersion tube, while the immersion tube is located in the first treatment position.

The measuring probe can, for example, be replaced while the process is running, preferably while the immersion tube is located in the second treatment position, since the gap between immersion tube and guiding passageway and therewith also the first and second treatment chambers are sealed in each position of the immersion tube relative to the process container.

In the second treatment position, the immersion tube and the measuring head can be washed, rinsed and sterilized. In such case, all sections of the immersion tube are washed, rinsed and sterilized, which are located within the first and second treatment chambers connected with one another.

In the first treatment position, the first treatment chamber is sealed both relative to the process container as well as also relative to the second treatment chamber. The first treatment chamber forms a relatively small space, into which opens supply- and drain lines for washing, and/or rinsing, medium, sterilization medium and/or calibration medium. Thus, an intensive washing, and/or rinsing, of the measurement head coupled with small liquid consumption is assured. In this treatment position, therefore, preferably the calibrating of the measuring probe is performed.

If the immersion tube is located in measuring position, then, for the case, in which there adjoins on the first section of the immersion tube with the first outer diameter, at its side facing away from the front end of the immersion tube, a third section of the immersion tube, which has relative to the first outer diameter a smaller, third outer diameter, so that through an axial shifting of the immersion tube into the measuring position, the second seal is opened, the second seal can be washed, rinsed and/or sterilized by supplying wash-, rinse- or sterilization medium into the first treatment chamber.

A first method currently considered as advantageous for operating the probe system, especially for the start-up of a new measuring probe, comprises the steps of:
- positioning the immersion tube in the second treatment position, wherein, in the second treatment position, the first treatment chamber is connected with the second treatment chamber, the first treatment chamber is sealed relative to the process container, and the measuring head is located within the first treatment chamber;
- securing a measuring probe within the immersion tube;
- shifting the immersion tube in the direction of the process connection until the the measuring position is reached, wherein, in the measuring position of the immersion tube, the measuring head is located within the process container, and the first treatment chamber is sealed relative to the second treatment chamber and is connected with the gap between the guiding passageway and the immersion tube in the region between the first treatment chamber and an additional seal sealing the gap relative to the process container;
- supplying a sterilization medium into the first treatment chamber and sterilizing the first treatment chamber, the therein arranged section of the immersion tube and the gap connected with the first treatment chamber;
- shifting the immersion tube in the direction facing away from the process connection, until reaching the first treatment position, wherein, in the first treatment position, the first treatment chamber is sealed relative to the second treatment chamber and relative to the process container, and the measuring head is located within the first treatment chamber;
- supplying a sterilization medium into the first treatment chamber and sterilizing the measuring head and the section of the protective cylinder surrounding the measuring head arranged within the first treatment chamber;
- supplying a sterilization medium into the process container and sterilizing the process container and the front region of the immersion tube in contact with the process container;
- shifting the immersion tube in the direction facing away from the process connection, until reaching the second treatment position;
- supplying a sterilization medium into the process container and sterilizing the process container and the front region of the immersion tube in contact with the process container and the section of the guiding passageway in contact with the process container through the shifting of the immersion tube into the second treatment position opened;

supplying a sterilization medium into the first and second treatment chambers connected with one another and sterilizing the sections of the immersion tube arranged in the first and second treatment chambers, the measuring head and the protective cylinder, as well as the seal between the first and the second treatment chambers opened through the shifting of the immersion tube into the second treatment position and accessible to the sterilization medium;

shifting the immersion tube in the direction of the process connection into the measuring position;

performing measurements by means of the measuring probe.

Optionally, after the sterilization steps and before shifting the immersion tube into the measuring position, the immersion tube can first be shifted into the first treatment position, calibration medium fed into the first treatment chamber and a calibrating of the measuring probe performed.

A second method currently considered advantageous for operating the probe system, especially for the start-up a new measuring probe, comprises the steps of:

positioning the immersion tube in the second treatment position, wherein in the second treatment position, the first treatment chamber is connected with the second treatment chamber, the first treatment chamber is sealed relative to the process container, and the measuring head is located within the first treatment chamber;

securing a measuring probe within the immersion tube;

supplying a sterilization medium into the first and second treatment chambers connected with one another and sterilizing the sections of the immersion tube, the measuring head and the protective cylinder arranged in the first and second treatment chambers, as well as the seal between the first and the second treatment chambers opened through the shifting of the immersion tube into the second treatment position and accessible to the sterilization medium;

supplying a sterilization medium into the process container and sterilizing the process container and the front region of the immersion tube in contact with the process container and the section of the guiding passageway in contact with the process container, opened through the shifting of the immersion tube into the second treatment position;

shifting the immersion tube into the first treatment position, wherein, in the first treatment position, the first treatment chamber is sealed relative to the second treatment chamber and relative to the process container, and the measuring head is located within the first treatment chamber;

supplying a sterilization medium into the first treatment chamber and sterilizing the section of the immersion tube arranged in the first treatment chamber and parts of the guiding passageway opened through movement of the immersion tube from the second treatment position into the first treatment position;

supplying a sterilization medium into the process container and sterilizing the process container and the front region of the immersion tube in contact with the process container and the regions of the protective cylinder in contact with the process container;

shifting the immersion tube in the direction of the process connection into the measuring position; and performing measurements by means of the measuring probe.

Optionally, after the sterilization steps and before shifting the immersion tube into the measuring position, the immersion tube can remain first in the first treatment position, calibration medium can be fed into the first treatment chamber and a calibrating of the measuring probe performed.

BRIEF DESCRIPTION OF THE DRAWINGS

The invention will now be explained in greater detail on the basis of the example of an embodiment illustrated in the drawing, the figures of the which show as follows:

FIG. 1 is a schematically shown, total view of the probe system in the first or second treatment positions;

FIG. 2a is a schematic, longitudinal, sectional representation of the probe system in the measuring position;

FIG. 2b is a detail view of the region characterized with a circle in FIG. 2a);

FIG. 3a is a schematic, longitudinal, sectional representation of the probe system in the first treatment position;

FIG. 3b is a detail view of the region characterized with a circle in FIG. 3a);

FIG. 4a is schematic, longitudinal, sectional representation of the probe system in the second treatment position; and FIG. 4b is a detail view of the region characterized with a circle in FIG. 4a).

DETAILED DISCUSSION IN CONJUNCTION WITH THE DRAWINGS

FIG. 1 shows a total view of the probe system 1. It includes a process connection 2, which in the present example is embodied as a connection nozzle, and which can be secured to a complementary connection nozzle 3 on the process container 4 (not shown in FIG. 1; compare FIGS. 2 to 4) by means of a union nut 5. Furthermore, the probe system 1 includes a probe body 6, which can be formed as one-piece or, as in the illustrated example, from a plurality of parts connected with one another. Within the probe body 6 is an axial guiding passageway 7 (not shown in FIG. 1; compare FIGS. 2-4), in which an immersion tube 8 is guided, which can be shifted axially in the direction of the process connection 2, or in the direction facing away from the process connection 2. Shifting of the immersion tube 8 is effected by an automatic, preferably pneumatic, drive apparatus 9, which is not described in detail here, whose operation, however, is known, for example, from DE 10 2005 051 279 A1. The drive apparatus 9 can also be embodied as described in the unpublished German patent application DE 10 2008 054884.7. Alternatively, shifting of the immersion tube can also occur by manual actuation.

The guiding passageway 7 includes a number of axial sections of different cross section. Within the probe body 6, there are, thus, between the guiding passageway 7 and the immersion tube 8, a first treatment chamber 10 and a second treatment chamber 11 adjoining the first treatment chamber 10 on a side of the first treatment chamber 10 facing away from the process connection 2, wherein the guiding passageway has, in the region of the treatment chambers 10, 11, sections with expanded cross section (compare also FIGS. 2-4). The guiding passageway is widened in the region of the first and second treatment chambers, in each case, in cross section. Introduced into the treatment chambers can be fluids, for example, liquids, vapor or gas, via fluid transport lines 15 opening into the treatment chambers (compare FIG. 2-4). The fluid transport lines 15 are embodied as bores within the probe body, which are connected with connection nozzles 12, 13 and 14 for connection to fluid-supply lines, such as, for example, hoses, pipes or tubes. Connection nozzles 12, 13, 14 and, correspondingly, the fluid transport lines 15 within the probe body are arranged on a side of an imaginary, longitudinal cutting plane through the probe body 6 extending not through the longitudinal axis A of the probe body 6, but, however, parallel thereto. This has the advantage, that the connection nozzles 12, 13, 14 are accessible from a single side of the probe system 1, so that the oppositely lying side remains free as installation space. On the whole, the probe system 1 requires, in this way, thus, less installation space than conventional probe systems, in the case of which the connection nozzles for washing, and/or rinsing, media are arranged on oppositely lying sides of the probe system.

The connection nozzles 12, 13, which are connected with fluid transport lines 15 opening into the first treatment chamber 10, and also the fluid transport lines themselves are inclined relative to the longitudinal axis A of the probe body 6, i.e. the bore axis B1 of each fluid transport line 15 coincides with the axis of the its connection nozzle 12, 13, and forms with the longitudinal axis A of the probe body 6 an acute angle α, preferably an angle α lying between 20° and 80°, whose apex points toward the process connection 2.

The connection nozzle 14, or the fluid transport line connected with it, extending as a bore within the probe body 6 and opening into the second treatment chamber (not shown in the longitudinal section) is likewise inclined relative to the longitudinal axis A of the probe body 6, or of the immersion tube 8. In such case, the bore axis B2 of the fluid transport line coincides with the axis of the connection nozzle 14 and forms with the longitudinal axis A an acute angle β, which preferably amounts to between 20° and 80°. The apex of angle β points away from the process connection 2.

In FIG. 2 *a*), the probe system 1 is shown in longitudinal section in the measuring position. FIG. 2 *b*) shows a detail view of the region marked by a circle in FIG. 2 *a*).

In the immersion tube 8 is held a measuring probe 16, which has on its end facing the front end 19 of the immersion tube 8 a measuring head 17 and on its end facing away from the front end 19 a probe plug head 18. Measuring head 17 comprises the primary measuring transducer of the measuring probe 16. The primary measuring transducer produces, correlated with the measured variable to be determined, a primary signal, which is forwarded to the measuring head 17 and therein, in given cases, converted by a there accommodated measuring electronics and transmitted from the measuring head 17 to a superordinated unit, for example, a measurement transmitter, connected mechanically with the plug head and, for example, galvanically, optically or inductively coupled, for signal- and energy transmission.

On its front end 19, the immersion tube 8 is formed into a protective cylinder 20 surrounding the measuring head 17. Spaced from the front end 19, protective cylinder 20 has a region with passageways in the form of washing, and/or rinsing, openings 21. The measuring probe 16 is held in such a manner in the immersion tube, that its measuring head 17 is arranged within the protective cylinder 20, and that a medium, in which the protective cylinder is immersed, comes through the washing, and/or rinsing, openings into contact with the measuring head 17.

The immersion tube 8 includes a number of sections with different outer diameters. A first section 22 possesses a first outer diameter. On the side of the first section 22 facing the front end 19 adjoins a second section 23, which has a second outer diameter, which is smaller than the outer diameter of the first section 22. Also, on the side of the first section 22 facing away from the front end 19 adjoins a third section 24, which has an outer diameter, which is smaller than the outer diameter of the first section 22. In the illustrated example, the outer diameters of the second section 23 and the third section 24 are equally large. On the side of the third section 24 facing away from the front end 19 adjoins a fourth section 25, which has a greater outer diameter than the second section 23 and the third section 24. The region between the front end 19 of the immersion tube and the second section 23, forms a fifth section 26, which extends between the front end 19 and the region with passageways in the form of the washing, and/or rinsing, openings 21. The outer diameter of the fifth section 26 is greater than the outer diameter of the second section 23. In the illustrated example, the outer diameters of the first section 22, the fourth section 25 and the fifth section 26 are equally large.

The outer diameters of the first section 22, the fourth section 25 and the fifth section 26 are so dimensioned, that they contact one or a number of sealing elements, which are arranged within the guiding passageway 7, and so form a seal, when one of the sections is located at a level with one of the sealing elements. The outer diameters of the second section 23 and the third section 24 are, in contrast, so dimensioned, that in the region of these sections there remains between the immersion tube 8 and the one or more sealing elements a gap, through which a fluid, which is introduced via the fluid transport lines 15 into the treatment chambers 10, 11, can pass.

Within the guiding passageway 7, in an annular groove, a first sealing element 27 is arranged between the first treatment chamber 10 and the second treatment chamber 11. A second sealing element 28 is arranged within the guiding passageway in an annular groove on the side of the first treatment chamber 10 facing the process connection 2. Between the process container 4 and the second sealing element 28, a third sealing element 29 is arranged in an annular groove in the guiding passageway 7 in the process-side end region of the connection nozzle 2. In the illustrated example, the sealing elements are embodied as O-rings; alternatively, the sealing elements could also be embodied as seals of other shapes. It is also possible to place the sealing elements on the immersion tube 8 instead of on the guiding passageway 7.

In the measuring position of the immersion tube 8 illustrated in FIGS. 2 *a*) and *b*), the protective cylinder with the measuring head 17 protrudes into the process container 4 filled with the fluid, whose measured variable is to be determined, so that the measuring head 17 comes in contact with the fluid via the washing, and/or rinsing, openings 21. In this position of the immersion tube, the first section 22 of the immersion tube lies with its end region facing away from the front end 19 against the third sealing element 29, so that the gap extending between the immersion tube 8 and the guiding passageway 7 on the side of the sealing element 29 facing away from the process container 4 is sealed relative to the process container 4. The third section 24 of the immersion tube 8 adjoining the first section 22 on the side of the first section 22 facing away from the front end 19, because of its smaller diameter, does not lie against the second sealing element 28, so that, in the measuring position, a gap is formed between the sealing element 28 and the section 24, through which a fluid contained in the first treatment chamber 10 situated on the side of the second sealing element 28 facing away from the process container 4 can penetrate. In the measuring position of the immersion tube, it is, therefore, possible, via the supply line 15, to introduce washing, and/or rinsing, liquid or a sterilization medium, e.g. superheated steam, and, in this way, to wash, and/or rinse, and to sterilize not only the first treatment chamber, but, instead also the sealing element 28 and the gap extending between the third section 24 of the immersion tube and the guiding passageway up to the sealing element 29.

In FIG. 3 a), the probe system 1 is shown in longitudinal sectional representation in the first treatment position. FIG. 3 b) shows a detail view of the region marked by a circle in FIG. 3 a).

In the first treatment position, the immersion tube 8 is retracted so far in the direction facing away from the process connection 2, that the measuring head 17 is located within the first treatment chamber 10. The fifth section 26 of the immersion tube 8 lies against the third sealing element 29 and the second sealing element 28, so that the gap between immersion tube 8 and guiding passageway 7 is sealed relative to the process container 4. Optionally, the first treatment position can be so selected, that the fifth section 26 of the immersion tube 8 does not also lie against the second sealing element 28.

The first section 22 of the immersion tube lies in the first treatment position against the first sealing element 27, so that the first treatment chamber 10 and the second treatment chamber 11 are sealed from one another. In this position, via the supply line 15, a washing, and/or rinsing, liquid, a calibration medium or a sterilization medium can be introduced into the first treatment chamber 10. The introduction occurs via a distribution canal 30, which enables a uniform flow onto the measuring head 17. Via the drain line (not shown in FIG. 2) connected with the connection nozzle 12, the medium supplied into the treatment chamber is drained away.

When the second sealing element 28 lies against the fifth section 26 of the immersion tube 8, the medium present in the first treatment chamber cannot penetrate into the gap between immersion tube 8 and guiding passageway 7 on the side of the so formed seal facing the process container 4. When the fifth section 26 of the immersion tube 8, however, is dimensioned short, or in the first treatment position does not lie against the sealing element 28, medium can flow past the sealing element 28 and fill the gap up to the sealing element 27. In this way, the sealing element 28 can be washed, rinsed and sterilized.

In FIG. 4 a), the probe system 1 is shown in longitudinal sectional representation in the second treatment position. FIG. 4 b) shows a detail view of the region marked by a circle in FIG. 4 a).

In the second treatment position, the immersion tube 8 is retracted relative to the first treatment position somewhat further in the direction facing away from the process connection 2. Due to the smaller (relative to the first section 22) diameter of the second section 23 of the immersion tube 8 adjoining the first section 22 of the immersion tube on the side of the first section 22 facing the front end 19, through shifting of the immersion tube 8 from the first treatment position into the second treatment position, a gap is opened between the second section 23 and the sealing element 27. This gap connects the first treatment chamber 10 and the second treatment chamber 11 with one another.

A seal 31 seals the second treatment chamber on its end facing away from the first treatment chamber 10. On the side of the first treatment chamber facing the process connection 2, the seal of the treatment chamber relative to the process container 4 is formed by the second sealing element 28 applied on the fifth section 26 of the immersion tube 8. In this position of the immersion tube, the third sealing element 29 is opened by the front end 19 of the immersion tube 8 being retracted therebehind, so that it is in contact with a medium located in the process container. In this position, therefore, a washing, cleaning and/or sterilizing of the third sealing element 29 and the opened region of the guiding passageway 7 is possible by introducing a cleaning- and/or sterilization medium into the process container 4.

A wash-, rinse- or sterilization medium introduced through the fluid transport line 15 into the first treatment chamber 10 is, due to the connection of the first and second treatment chambers in the second treatment position of the immersion tube 8, accessible to all regions of the immersion tube 8 and the measuring probe 16 contained in the first and second treatment chambers 10, 11. The medium can be fed, instead of through the fluid transport line 15, also through the supply line 14 opening into the second treatment chamber 11. Advantageously, one of the fluid transport lines opening into the first treatment chamber 10 is closed by means of a valve (not shown). Via the supply line 14, which is shown only in FIG. 1, not, however, in the longitudinal section in FIG. 4, a wash- and/or rinse- or sterilization medium can be charged into the second treatment chamber 11 and drained via the fluid transport line 15 out of the first treatment chamber.

In order in the case of the probe system 1 described on the basis of FIGS. 1 to 4, to perform a replacement of the measuring probe and a following sterilization of the new measuring probe 16 and the, in the case of replacement, in given cases, contaminated immersion tube 8, procedure can be, for example, as will now be related.

In a first variant, first, the immersion tube 8 is shifted into the second treatment position (FIG. 4). In the second treatment position, the new measuring probe 16 is installed into the immersion tube 8. Then, the immersion tube 8 is shifted into the measuring position (FIG. 2). In the first treatment chamber 10, a sterilization medium is introduced and the first treatment chamber 10 sterilized, along with the gap between the treatment chamber and the sealing element 29. Thereafter, the immersion tube 8 is shifted into the first treatment position (FIG. 3). In this position, the section 22 of the immersion tube 8 lies against the sealing element 27, so that the first treatment chamber is sealed from the second treatment chamber. Into the first treatment chamber, now a sterilization medium is introduced. At the same time, or, thereafter, in the process container 4, a sterilization medium is introduced, in order to sterilize the front end 19 of the immersion tube 8 and the process container 4. Then, the immersion tube is shifted anew into the second treatment position. In this position, again a sterilizing of the process container 4 is performed, wherein in the second treatment position of the immersion tube 8 also the sealing element 29 for the process container 4 lies exposed, so that also sealing element 29 is sterilized. Thereafter, into the first and second treatment chambers 10, 11, which are connected with one another in the second treatment position by a gap in the region of the opened sealing element 27, a sterilization medium is introduced and a sterilizing performed of all parts arranged in the treatment chambers 10, 11, especially also the sealing element 27. Then, the immersion tube 8 can either immediately be moved into the measuring position, or first likewise into the first treatment position, in which a calibrating of the measuring probe 16 can be performed by supplying calibration medium into the first treatment chamber 10. After the calibrating, the immersion tube can then be moved into the measuring position.

In a second variant, first the immersion tube 8 is shifted into the second treatment position and the new measuring probe 16 placed in the immersion tube 8. Thereafter, the immersion tube 8 remains first in the second treatment position, wherein a sterilization medium is introduced into the treatment chambers 10, 11 connected with one another and a sterilizing performed of all parts arranged in the two treatment chambers, as well as the sealing element 27. In the next step, or simultaneously, in the process container 4 likewise a sterilization medium can be introduced and a sterilizing of the process container 4, the sealing element 29 and the end region of the guiding passageway 7, as well as the front end 19 of the immersion tube performed. This is, however, only required at first startup of the measuring point. In running measurement operation, the process container and the parts of the probe system 1 in contact with it remain sterile, when the measuring probe 16 is replaced in the second treatment position of the immersion tube. Then, the immersion tube is shifted into the first treatment position. In this position, sterilization medium is introduced into the first treatment chamber and a sterilizing performed. In the case of first startup of the measuring point, then the immersion tube 8 is further shifted in the direction of the process container 4, so that at least the end region of the protective cylinder 20, i.e. the section 26 of the immersion tube, protrudes inwardly into the process container. This end region can then be sterilized by supplying a sterilization medium into the process container 4.

For performing the sterilization steps, the probe system 1 and the process container 4 are heatable and may be placed under pressure. Sensors can be placed on the supply and drain lines for wash-, rinse-, calibration and sterilization media, which monitor the purity of the mentioned media, in order so, especially, to check the sterilization of the probe system.

The invention claimed is:

1. A probe system for measuring a measured variable of a fluid, especially a liquid, contained in a process container, comprising:
   a probe body, which is connectable to the process container by means of a process connection;
   an immersion tube axially shiftable in a guiding passageway of the probe body between a measuring position and at least two different treatment positions, said immersion tube, having a front end and a protective cylinder on said front end immersible in the fluid;
   a measuring probe held in the immersion tube, said measuring probe having a measuring head, wherein said measuring head is arranged within a region of said protective cylinder having openings;
   a first treatment chamber formed between said guiding passageway and said immersion tube;
   a second treatment chamber formed between said guiding passageway and said immersion tube, and adjoining said first treatment chamber on a side of said first treatment chamber facing away from said process connection;
   a seal arranged between said first and said second treatment chambers; and
   at least two fluid transport lines, which open into said first treatment chamber, of which one serves as a supply line and another as a drain line, as well as one other fluid transport line opening into said second treatment chamber and selectively serving as a supply line or as a drain line; wherein:
   said immersion tube has a first section with a first outer diameter and a second section adjoining said first section and having a second outer diameter smaller, than the first outer diameter, so that, by axial shifting of the immersion tube, the seal arranged between the first and the second treatment chambers can be opened.

2. The probe system as claimed in claim 1, wherein:
   said second section adjoins said first section in the direction of said front end of said immersion tube;
   in a first treatment position of said immersion tube, said seal seals said first treatment chamber and said second treatment chamber from one another;
   in the case of an axial shifting movement of said immersion tube in a direction facing away from said process connection into a second treatment position, said seal is opened and a fluid passageway forms between said first and said second treatment chambers.

3. The probe system as claimed in claim 2, wherein:
   said seal is formed arranged within said guiding passageway by a sealing element, which, in said first treatment position of said immersion tube, lies against said first section with said first outer diameter.

4. The probe system as claimed in claim 3, wherein:
   in said second treatment position, between said sealing element and said second section of said immersion tube, due to the smaller second outer diameter relative to the first outer diameter, a gap is opened, which connects said first treatment chamber and said second treatment chamber with one another.

5. The probe system as claimed in claim 1, wherein:
   each fluid transport line, which opens into said first treatment chamber, is closable by means of a valve.

6. A method for operating a probe system as claimed in claim 1, whose immersion tube can be shifted axially into a measuring position, a first treatment position and a second treatment position, comprising steps of:
   shifting the immersion tube into the second treatment position, in which the seal between the first and the second treatment chamber is opened, so that the first and second treatment chamber are connected with one another;
   securing a measuring probe within the immersion tube, while the immersion tube is located in the second treatment position; and further comprising at least one of the following steps:
   supplying a sterilization medium into the connected treatment chambers and sterilizing the sections of the immersion tube located within the first and second treatment chambers and the measuring head of the measuring probe accessible via washing, and/or rinsing, openings within the protective cylinder on the front end of the immersion tube while the immersion tube is located in the second treatment position;
   supplying a sterilization medium into the first treatment chamber and sterilizing the section of the immersion tube located within the first treatment chamber and the measuring head of the measuring probe accessible via the washing, and/or rinsing, openings within the protective cylinder on the front end of the immersion tube while the immersion tube is located in the first treatment position, in which the first and the second treatment chamber are sealed from one another;
   supplying a washing, and/or rinsing, liquid into the first treatment chamber and washing and/or rinsing the section of the immersion tube located within the first treatment chamber and the measuring head of the measuring probe accessible via the washing, and/or rinsing, openings within the protective cylinder on the front end of the immersion tube while the immersion tube is located in the first treatment position; and
   supplying a calibration liquid into the first treatment chamber and calibrating the measuring probe, whose measuring head is supplied with calibration liquid via the washing, and/or rinsing, openings within the protective cylinder on the front end of the immersion tube, while the immersion tube is located in the first treatment postion.

7. A probe system for measuring a measured variable of a fluid, especially a liquid, contained in a process container, comprising:
   a probe body, which is connectable to the process container by means of a process connection;
   an immersion tube axially shiftable in a guiding passageway of the probe body between a measuring position and at least first and second different treatment positions, said immersion tube, having a front end and a protective cylinder on said front end immersible in the fluid;

a measuring probe held in the immersion tube, said measuring probe having a measuring head, wherein said measuring head is arranged within a region of said protective cylinder having openings;

a first treatment chamber formed between said guiding passageway and said immersion tube;

a second treatment chamber formed between said guiding passageway and said immersion tube, and adjoining said first treatment chamber on a side of said first treatment chamber facing away from said process connection; and a seal arranged between said first and said second treatment chambers; wherein:

said immersion tube has a first section with a first outer diameter and a second section adjoining said first section and having a second outer diameter smaller, than the first outer diameter, so that, by axial shifting of the immersion tube, the seal arranged between the first and second treatment chambers can be opened;

on the side of said first treatment chamber facing said process connection, a second seal is arranged, which seals said first treatment chamber relative to said process container, when said immersion tube is located in said second treatment position; and spaced from said second seal on said process connection side end region of said probe body, a third seal is arranged, which seals said guiding passageway and said first treatment chamber relative to said process container, when said immersion tube is located in said measurig position or in said first treatment position.

8. The probe system as claimed in claim 7 wherein:

adjoining said first section of said immersion tube with the first outer diameter on its side facing away from said front end of said immersion tube, is a third section of said immersion tube, which has a third outer diameter smaller than said first outer diameter; and said third outer diameter, especially, is equally as large as said second outer diameter, so that, by axial shifting of said immersion tube in the direction of said process connection into said measuring position, said second seal is opened.

9. The probe system as claimed in claim 8, wherein:

said second seal is formed arranged within the guiding passageway by a second sealing element, which, in said second treatment position, lies against said first section of said immersion tube, while in said measuring position of said immersion tube, between said second sealing element and said third section of said immersion tube, due to said first outer diameter being smaller than said third outer diameter, a gap is present, which makes said second sealing element accessible for liquid supplied via said supply line into said first treatment chamber.

\* \* \* \* \*